United States Patent
Steinbrenner et al.

(10) Patent No.: US 6,284,704 B1
(45) Date of Patent: Sep. 4, 2001

(54) PREPARATION OF A BASIC CATALYST AVOIDING HIGH TEMPERATURES

(75) Inventors: Ulrich Steinbrenner, Ludwigshafen (DE); Eugen Gehrer, Rankweil (AT)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/407,284

(22) Filed: Sep. 29, 1999

(30) Foreign Application Priority Data

Oct. 1, 1998 (DE) .............................................. 198 45 293

(51) Int. Cl.$^7$ .............................. B01J 23/02; B01J 23/48; B01J 23/18; B01J 23/54
(52) U.S. Cl. ......................... 502/344; 502/183; 502/184; 502/303; 502/340; 502/341; 502/342; 502/343; 502/347; 502/348
(58) Field of Search .................................... 502/183, 184, 502/303, 340, 341, 342, 343, 344, 347, 348

(56) References Cited

U.S. PATENT DOCUMENTS

| | | | |
|---|---|---|---|
| 4,226,782 | * 10/1980 | Hayden et al. | 502/344 |
| 4,914,250 | 4/1990 | Smith | 585/452 |
| 4,922,054 | 5/1990 | Smith | 585/452 |

FOREIGN PATENT DOCUMENTS

| | | |
|---|---|---|
| 439679 | 8/1991 | (EP) . |
| 05163171 | 12/1991 | (JP) . |

* cited by examiner

Primary Examiner—Elizabeth D. Wood
(74) Attorney, Agent, or Firm—Keil & Weinkauf

(57) ABSTRACT

A catalyst comprising at least one alkali metal and at least one metallic or semimetallic promoter selected from the group consisting of Ca, Sr, Ba, Ag, Au, Zn, Cd, Hg, In, Tl, Sn, As, Sb and Bi, on a support which may be doped with one or more compounds of an alkali metal and/or alkaline earth metal, where the alkali metal/support ratio by weight is from 0.01 to 5, the promoter/alkali metal ratio by weight is from 0.0001 to 5 and, when a dopant is present, the dopant/support ratio by weight is from 0.01 to 5.

4 Claims, No Drawings

PREPARATION OF A BASIC CATALYST AVOIDING HIGH TEMPERATURES

FIELD OF THE INVENTION

The invention relates to a catalyst, to a process for preparing it, to its use in reactions catalyzed by strong bases, and to a process for side-chain alkylation or side-chain alkenylation of alkylaromatic compounds with olefins or diolefins.

The side-chain alkylation of aromatic compounds which have an acidic proton in the α position of the side chain in the presence of basic catalysts is known. Known basic catalysts consist of a support, which may be doped with one or more compounds of an alkali metal and/or alkaline earth metal, and an alkali metal or an alkali metal alloy as active component.

PRIOR ART

EP-B 0 439 679 describes a process for the alkylation of alkylaromatic hydrocarbons. The reaction takes place in the presence of an activated alumina catalyst which is doped with magnesium hydroxide and potassium metal. Also used in place of magnesium hydroxide are calcium hydroxide, barium hydroxide or magnesium oxide. Impregnation with potassium hydride is also described.

U.S. Pat. No. 4,914,250 relates to a process for the side-chain alkylation of aromatic compounds. The catalyst employed in this case is diatomaceous earth which is present in the reaction mixture in addition to potassium or NaK and traces of water.

U.S. Pat. No. 4,922,054 likewise relates to a process for the side-chain alkylation of aromatic compounds, in which diatomaceous earth is likewise employed as catalyst, which is present in the reaction mixture in addition to Nay and potassium oxide. Rubidium oxide is also used in place of potassium oxide. Potassium metal is also employed in place of NaK.

JP-A2 05163171 relates to the preparation of alkenylbenzene and its derivatives. The catalyst used comprises an alkali metal and a potassium carbonate salt and/or KOH, which are dispersed in the presence of an olefin and/or diolefin. Sodium metal is preferably employed as alkali metal, and $K_2CO_3$, $KHCO_3$ or $KNaCO_3$ is preferably employed as potassium carbonate salt.

Application of the alkali metal or the alkali metal alloy as active component to the doped catalyst support takes place only poorly at temperatures markedly below 300° C. because then there is scarcely any wetting of the support by the metal. The catalysts obtained in this way have only low activity, i.e. the space-time yield is very low. On the other hand, it is desirable to carry out the catalyst preparation in the same reaction vessel in which the side-chain alkylation will later be carried out. This makes it possible to dispense with a transfer of the air-sensitive, pyrophoric catalyst. However, many reaction apparatuses are operated with steam or oil heating and are not designed for temperatures around 300° C. Even at temperatures around 300° C. there is a not inconsiderable amount of vaporization of alkali metal, which may lead to corrosion problems.

SUMMARY OF THE INVENTION

It is an object of the present invention to provide a basic catalyst of an alkali metal as active component on a support for the side-chain alkylation of alkylaromatic compounds, which can be prepared at temperatures markedly below 300° C. and is distinguished by a high activity.

We have found that this object is achieved by a catalyst comprising at least one alkali metal and at least one metallic or semimetallic promoter selected from the group consisting of Ca, Sr, Ba, Ag, Au, Zn, Cd, Hg, In, Tl, Sn, As, Sb and Bi, on a support which may be doped with one or more compounds of an alkali metal and/or alkaline earth metal, where the alkali metal/support ratio by weight is from 0.01 to 5, the promoter/alkali metal ratio by weight is from 0.0001 to 5 and, when a dopant is present, the dopant/support ratio by weight is from 0.01 to 5.

The object is also achieved by using this catalyst in reactions catalyzed by strong bases, preferably for the side-chain alkylation or side-chain alkenylation of alkylaromatic compounds with olefins or for the double-bond isomerization of olefins, for the dimerization of olefins or for the basic amination of olefins.

The object is further achieved by way of example by providing a process for the side-chain alkylation or side-chain alkenylation of alkylaromatic compounds by reaction with olefins or diolefins, the reaction being carried out in the presence of a catalyst defined above.

DETAILED DESCRIPTION OF THE INVENTION

The wetting properties of the liquid alkali metal are distinctly improved by the addition of a metallic or semimetallic promoter which dissolves noticeably in the liquid alkali metal at temperatures below 300° C.

The alkali metal/support ratio by weight is in this case preferably from 0.01 to 2, particularly preferably from 0.01 to 1. The alkali metal is in this case preferably sodium or potassium, in particular sodium. It is also possible to employ mixtures of several alkali metals. A preferred mixture is a sodium/potassium alloy.

The promoter/alkali metal ratio by weight is preferably from 0.0001 to 1, particularly preferably from 0.0001 to 0.3, in particular 0.01 to 0.1. Preferred promoters are Ca, Sr, Ba, Zn, In, Sn, Sb, particularly preferably Ca, Sr, Ba and Zn. Mixtures of several promoters can also be employed.

Catalyst supports are conventional supports such as $Al_2O_3$, $La_2O_3$, $ZrO_2$, graphite, diatomaceous earth, spinels, inverse spinels, alkaline earth metal oxides, alkali metal carbonates, alkaline earth metal carbonates, titanates, zirconates and hafnates.

The support may moreover be doped with at least one compound of an alkali metal and/or alkaline earth metal in the dopant/support ratio by weight of from 0.01 to 5, preferably 0.01 to 2, in particular 0.01 to 1. The catalyst is preferably doped in this way. In this case, the supports are preferably doped with soluble compounds of the alkali metals and/or alkaline earth metals, such as the oxides, hydroxides, carbonates, formates, acetates, oxalates and/or hydrides. Preference is given to the use of the hydroxides or carbonates, and particular preference to $K_2CO_3$ and/or KOH.

The catalysts are prepared by
applying to the support at least one alkali metal and at least one metallic or semimetallic promoter in the form of a solution of the promoter in the molten alkali metal, the support having, where appropriate, previously been doped by impregnation with a solution of at least one compound of an alkali metal and/or alkaline earth metal, drying and calcining the doped support.

The alkali metal and the metallic or semimetallic promoter are applied in the molten state to the support. The application to the support takes place at a temperature preferably of from 80 to 400° C., particularly preferably of from 100 to 200° C. To do this, the appropriate amount of the alkali metal in the form of a ribbon or block is added together with the appropriate amount of the promoter in elemental form to the support and mixed therewith while heating. It is also possible to add an alloy, an intermetallic phase or compound of the alkali metal with the promoter as ribbon, block, granules or powder. When the solution of the promoter in the molten alloy metal is mixed with the support, the alkali metal becomes finely dispersed on the support. The application of the alkali metals to the support can take place in vacuo, under an inert gas atmosphere (He, $N_2$, Ar etc.) or under a reactive gas atmosphere ($H_2$, $CO_2$, CO).

The doping of the support takes place in a manner known per se by impregnation and subsequent calcination at temperatures in the range from 100 to 1500° C., preferably 250 to 1000° C., particularly preferably 250 to 350° C. The impregnation with a solution of the compound of the alkali metal and/or alkaline earth metal can moreover take place in any suitable solvent. Aqueous solutions are preferably employed, in which case the water is removed after the impregnation by drying the impregnated support. Calcination is also possible without previous drying, in which case the solvent escapes at the start of the calcination. Calcination of the doped support can be carried out under reduced pressure, under atmospheric pressure or under elevated pressure. It can moreover take place either in an oxygen-containing atmosphere or in an inert gas atmosphere such as under helium, nitrogen or argon, or under a reactive gas atmosphere, such as under hydrogen, ammonia, carbon dioxide or carbon monoxide.

The catalysts are employed in reactions catalyzed by strong bases, preferably for the side-chain alkylation or side-chain alkenylation of alkylaromatic compounds with olefins or diolefins, for the double-bond isomerization of olefins, for the dimerization of olefins or for the basic amination of olefins.

The reaction is generally carried out at a temperature of from −50 to 400° C., preferably at a temperature of from −20 to 300° C., particularly preferably 80 to 250° C., in particular 100 to 220° C. and under a pressure of, preferably, from 0.1 to 200, particularly preferably 1 to 150, in particular 1 to 100 bar.

It is possible in this connection to employ all suitable alkylaromatic compounds. They may have a benzene or naphthalene nucleus, for example, as aromatic nucleus. It is also possible to employ residues in which a plurality of the ring structures are linked together. The ring structures have an acidic hydrogen atom in the a position of the side chain. They preferably have at least one alkyl radical which is bonded to the cyclic structure. The alkyl radicals may in this connection have any length and be substituted by other substituents. Alkylaromatic compounds preferably employed are benzenes substituted by 1 to 6, preferably 1 to 3, in particular 1 to 2, $C_{1-20}$-, preferably $C_{1-3}$-alkyl radicals.

The olefins preferably have 2 to 20, particularly preferably 2 to 10, in particular 2 to 5, C atoms. Preferably employed are ethene, propene, 1-butene, 2-butene, isobutene, 1-pentene, 2-pentene, 2-methyl-1-butene, 2-methyl-2-butene and/or 3-methyl-1-butene. Ethene and propene are particularly preferred. The diolefins preferably have 4 to 20, particularly preferably 4 to 10, in particular 4 to 6, C atoms. Butadiene and/or isoprene are particularly preferably employed.

Examples of olefins which can be isomerized or dimerized with the catalyst according to the invention are the abovementioned olefins. Olefins which can be aminated with the catalysts according to the invention are, in particular, ethene or conjugated dienes such as butadiene or isoprene, and the amines preferably employed are ammonia, diethylamine, ethylamine, diisopropylamine or pyrrolidine.

Particular preference is given to the reaction of toluene with ethene or propene to give propylbenzene or isobutylbenzene, the reaction of cumene with ethene to give tert-amylbenzene and the reaction of xylenes with butadiene to give 5-tolylpentenes, and the reaction of p-xylene with 1-butene or 2-butene to give 1-tolyl-2-methylbutane.

The reaction can be carried out batchwise or, preferably, continuously in the liquid or gas phase, preferably in the liquid phase. It is moreover possible to employ known apparatus for carrying out the process.

The invention is illustrated further below by means of examples.

EXAMPLES

Preparation Examples

At the end of each example, the elemental analyses per 100 g of the doped support before application of the alkali metal are indicated in parentheses.

Catalyst A (Comparative)

10 g of γ-$Al_2O_3$ were impregnated with 1 g of $K_2CO_3$ (dissolved in $H_2O$). The suspension was evaporated to dryness, and the powder obtained in this way was calcined at 300° C. while stirring in a stream of argon for 15 hours. 1 g of metallic sodium were added to this powder and dispersed at 160° C. for 2 hours.

Catalyst B

Preparation as for catalyst A but employing 1 g of an alloy of 49% by weight barium and 51% by weight sodium in place of sodium.

Catalyst C

Preparation as for catalyst A but employing 1 g of an alloy of 6% by weight barium and 94% by weight sodium in place of sodium.

Catalyst D

Preparation as for catalyst A with addition of 0.1 g of Sn.

Catalyst E

Preparation as for catalyst A with addition of 0.1 g of Pb.

Catalyst F

Preparation as for catalyst A with addition of 0.1 g of Tl.

Catalyst G

Preparation as for catalyst A with addition of 0.1 g of Ca.

Catalyst H

Preparation as for catalyst A with addition of 0.1 g of Sr.

Process Examples

Comparative Example C1

10 g of catalyst A were introduced with 85 g of toluene into a pressure-tight reaction vessel. After addition of 20 g of propene, the reaction vessel was heated to 160° C., and the reaction suspension was then stirred for 12 hours. The results are listed in the table.

Examples 1 to 7

10 g in each case of catalyst B to H were introduced with 85 g of toluene into a pressure-tight reaction vessel. After addition of 20 g of propene, the reaction vessel was heated to 160° C., and the reaction suspension was then stirred for 12 hours. The results are listed in the table (all data in mol%).

| Ex. | Catalyst | $C_{propene}$ | $S_{iBB}^*$ | $S_{MP}$ | $C_{Toluene}$ | $S_{iBB}^{**}$ |
|---|---|---|---|---|---|---|
| C1 | A | 23 | 51 | 44 | 6 | 91 |
| 1 | B | 37 | 56 | 39 | 11 | 92 |
| 2 | C | 32 | 61 | 32 | 11 | 90 |
| 3 | D | 33 | 57 | 38 | 10 | 91 |
| 4 | E | 50 | 58 | 38 | 16 | 93 |
| 5 | F | 52 | 55 | 40 | 23 | 93 |
| 6 | G | 51 | 59 | 37 | 16 | 93 |
| 7 | H | 64 | 57 | 38 | 20 | 93 |

$C_{propene}$ = propene conversion [mol %]
$S_{iBB}^*$ = selectivity for isobutylbenzene based on propene [mol %]
$S_{MP}$ = selectivity for methylpentene based on propene [mol %]
$S_{iBB}^{**}$ = selectivity for isobutylbenzene based on toluene [mol %]
$C_{Toluene}$ = toluene conversion [mol %]

We claim:

1. A catalyst comprising at least (1) one alkali metal and (2) at least one metallic or semimetallic promoter selected from the group consisting of Ca, Sr, Ba, Ag, Au, Zn, Cd, Hg, In, Tl, Sn, As, Sb and Bi, on (3) a support which is optionally doped with (4) one or more alkali metal and/or alkaline earth metal compounds, where the alkali metal (1)/support (3) ratio by weight is from 0.01 to 5, the promoter (2)/alkali metal (1) ratio by weight is from 0.0001 to 5 and, when a dopant is present, the dopant (4)/support (3) ratio by weight is from 0.1 to 5, and wherein the alkali metal (1) is finely dispersed in metallic form on the support.

2. A catalyst as claimed in claim 1, wherein the support is selected from the group consisting of $Al_2O_3$, $La_2O_3$, $ZrO_2$, graphite, diatomaceous earth, spinels, inverse spinels, alkaline earth metal oxides, alkali metal carbonates, alkaline earth metal carbonates, titanates, zirconates and hafnates.

3. A catalyst as claimed in claim 1, wherein the support is doped with at least one hydroxide or carbonate of an alkali metal and/or alkaline earth metal (4).

4. A process for preparing catalysts as defined in claim 1 by applying to the support (3) at least one alkali metal (1) and at least one metallic or semimetallic promoter (2) in the form of a solution of the promoter (2) in the molten alkali metal (1), the support (3) having optionally, previously been doped by impregnation with a solution of at least one compound of an alkali metal and/or alkaline earth metal (4), drying and calcining the doped support.

* * * * *